(12) United States Patent
Bryan

(10) Patent No.: US 6,872,196 B1
(45) Date of Patent: Mar. 29, 2005

(54) ABDOMINAL DEFECT COVER DEVICE

(76) Inventor: Judith L. Bryan, 15006 One-O-One Trail, Amarillo, TX (US) 79118

(*) Notice: Subject to any disclaimer, the term of this patent is extended or adjusted under 35 U.S.C. 154(b) by 51 days.

(21) Appl. No.: 10/266,948

(22) Filed: Oct. 9, 2002

(51) Int. Cl.⁷ ............................................. A61F 13/00
(52) U.S. Cl. ...................... 604/305; 604/304; 604/290; 604/23
(58) Field of Search .................. 604/304, 305–308, 604/128, 202.1, 23, 25, 290; 128/202.12

(56) References Cited

U.S. PATENT DOCUMENTS

| | | | | |
|---|---|---|---|---|
| 3,026,874 A | * | 3/1962 | Stevens | 604/305 |
| 3,874,387 A | * | 4/1975 | Barbieri | 602/53 |
| 4,474,571 A | * | 10/1984 | Lasley | 604/23 |
| 4,717,382 A | * | 1/1988 | Clemens et al. | 604/122 |
| 5,263,922 A | * | 11/1993 | Sova et al. | 602/59 |
| 6,432,077 B1 | * | 8/2002 | Stenzler | 604/23 |
| 2002/0161345 A1 | * | 10/2002 | McMillin | 604/304 |

* cited by examiner

Primary Examiner—Jacqueline F. Stephens

(57) ABSTRACT

An abdominal defect cover device for protecting undeveloped and defective regions of the abdomen of a newborn, in particular. The abdominal defect cover device includes a domed-shaped cover member having an opening being centrally-disposed therethrough; an also includes a valve assembly being securely disposed in the opening for allowing introduction of a saline solution upon a user's abdomen; and further includes a seal being attached to the dome-shaped cover member for sealing the dome-shaped cover member upon the user's abdomen; and also includes a fastening assembly for fastening and holding the dome-shaped cover member upon the user's abdomen.

3 Claims, 4 Drawing Sheets

ABDOMINAL DEFECT COVER DEVICE

BACKGROUND OF THE INVENTION

1. Field of the Invention

The present invention relates to abdomen defect covers and more particularly pertains to a new abdominal defect cover device for protecting undeveloped and defective regions of the abdomen of a newborn, in particular.

2. Description of the Prior Art

The use of abdomen defect covers is known in the prior art. More specifically, abdomen defect covers heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. No. 3,561,442; U.S. Pat. No. 4,190,054; U.S. Pat. No. 4,577,591; U.S. Pat. No. 5,439,456; U.S. Pat. No. 4,378,010; U.S. Pat. No. 4,116,197; U.S. Pat. No. 5,380,312; U.S. Pat. No. 4,568,339; and U.S. Pat. No. Des. 318,922.

While these devices fulfill their respective, particular objectives and requirements, the aforementioned patents do not disclose a new abdominal defect cover device. The prior art includes pouches and straps for placing over certain parts of a user's body and also includes bandages for covering certain effected parts of the user's body.

SUMMARY OF THE INVENTION

The general purpose of the present invention, which will be described subsequently in greater detail, is to provide a new abdominal defect cover device which has many of the advantages of the abdomen defect covers mentioned heretofore and many novel features that result in a new abdominal defect cover device which is not anticipated, rendered obvious, suggested, or even implied by any of the prior art abdomen defect covers, either alone or in any combination thereof. The present invention includes a domed-shaped cover member having an opening being centrally-disposed therethrough; an also includes a valve assembly being securely disposed in the opening for allowing introduction of a saline solution upon a user's abdomen; and further includes a seal being attached to the dome-shaped cover member for sealing the dome-shaped cover member upon the user's abdomen; and also includes a fastening assembly for fastening and holding the dome-shaped cover member upon the user's abdomen. None of the prior art includes the combination of the elements of the present invention.

There has thus been outlined, rather broadly, the more important features of the abdominal defect cover device in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

It is an object of the present invention to provide a new abdominal defect cover device which has many of the advantages of the abdomen defect covers mentioned heretofore and many novel features that result in a new abdominal defect cover device which is not anticipated, rendered obvious, suggested, or even implied by any of the prior art abdomen defect covers, either alone or in any combination thereof.

Still another object of the present invention is to provide a new abdominal defect cover device for protecting undeveloped and defective regions of the abdomen of a newborn, in particular.

Still yet another object of the present invention is to provide a new abdominal defect cover device that is easy and convenient to set up and use.

Even still another object of the present invention is to provide a new abdominal defect cover device that prevents the onset of infection in the wall lining of a newborn's abdomen.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
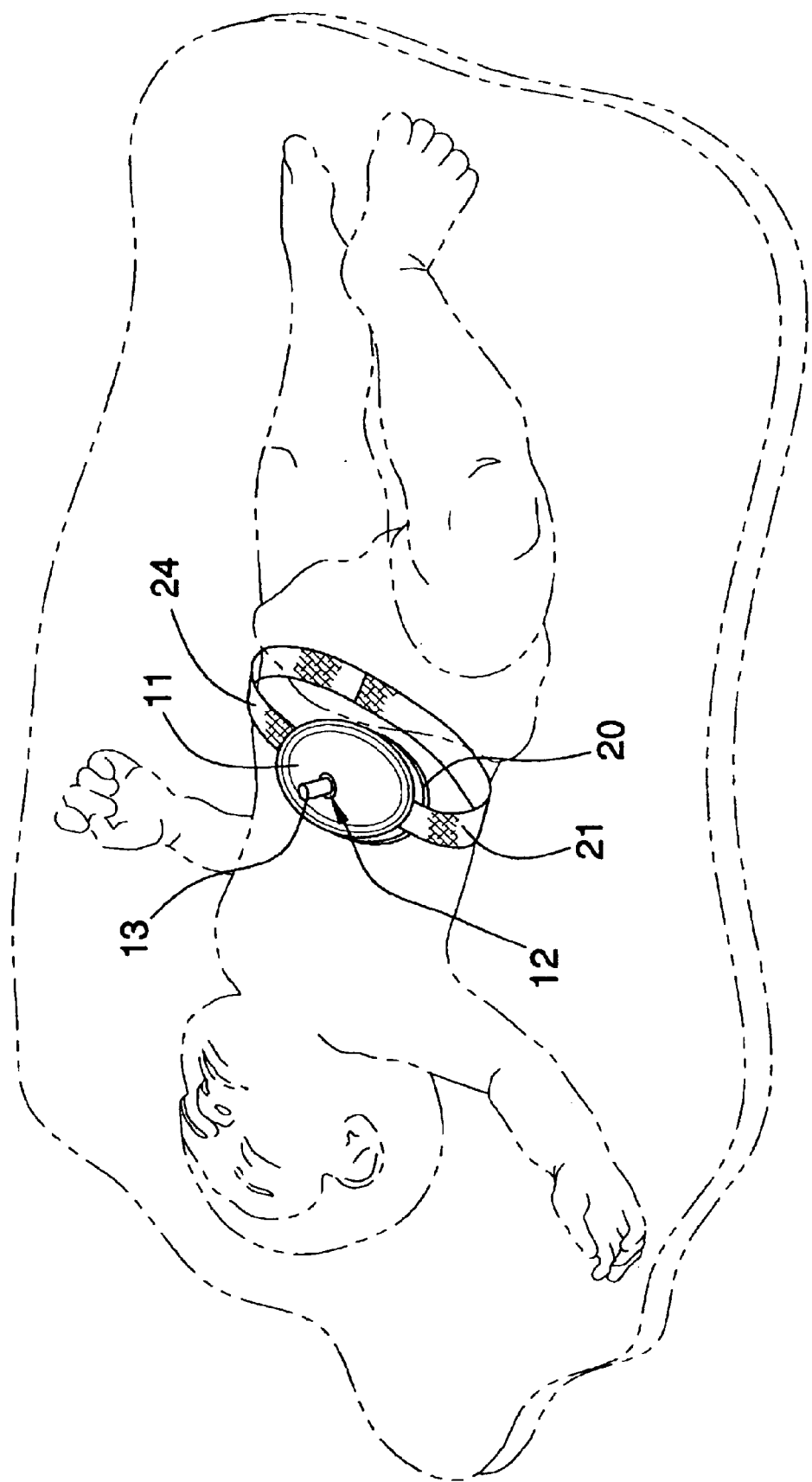
FIG. 1 is a perspective view of a new abdominal defect cover device according to the present invention.
Figure 2:
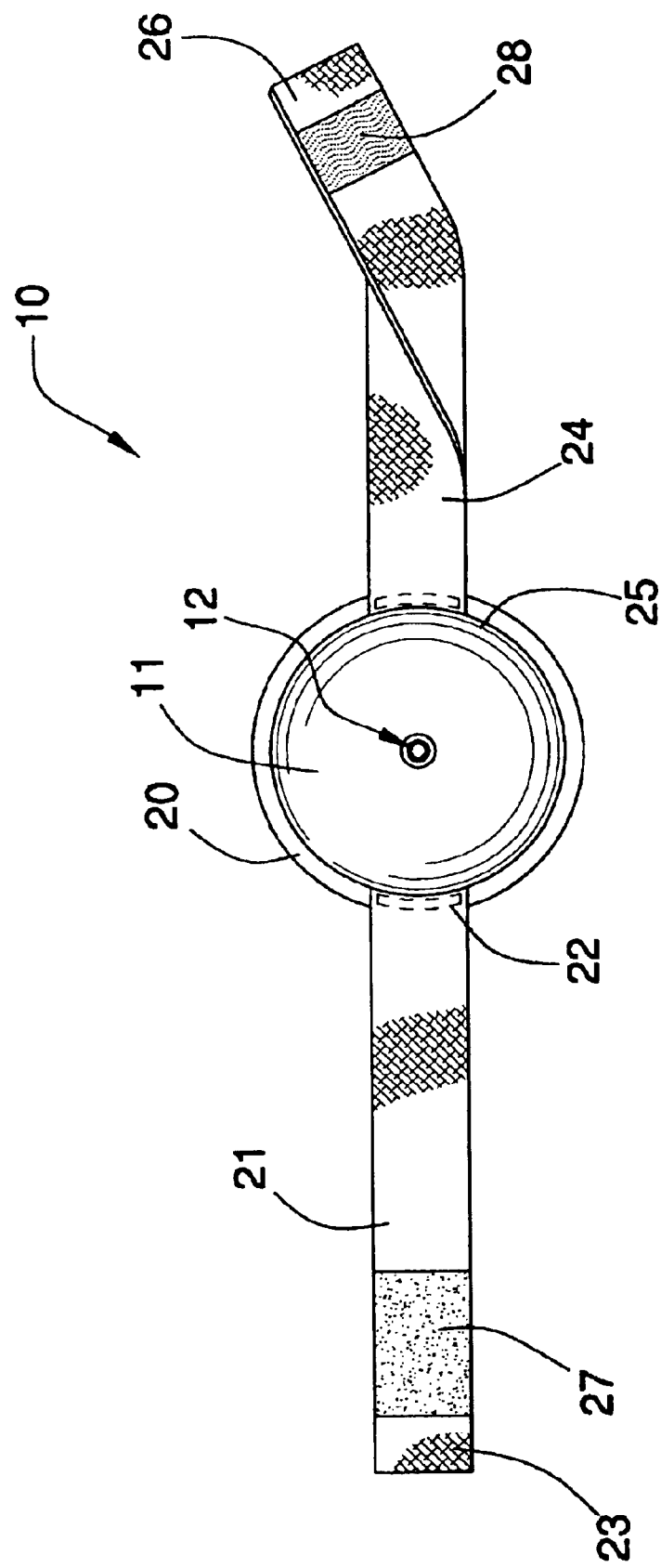
FIG. 2 is a top plan view of the present invention.
Figure 3:
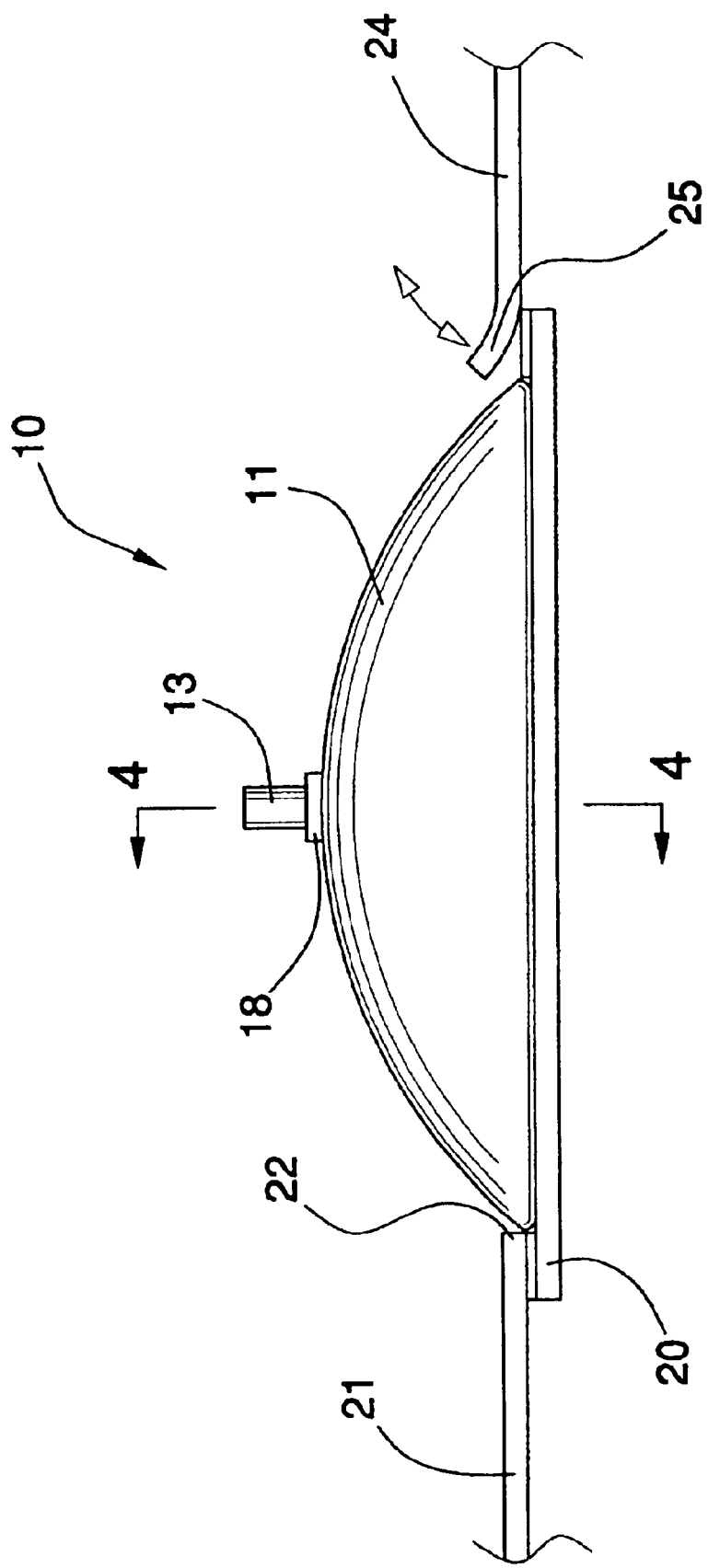
FIG. 3 is a side elevational view of the present invention.
Figure 4:
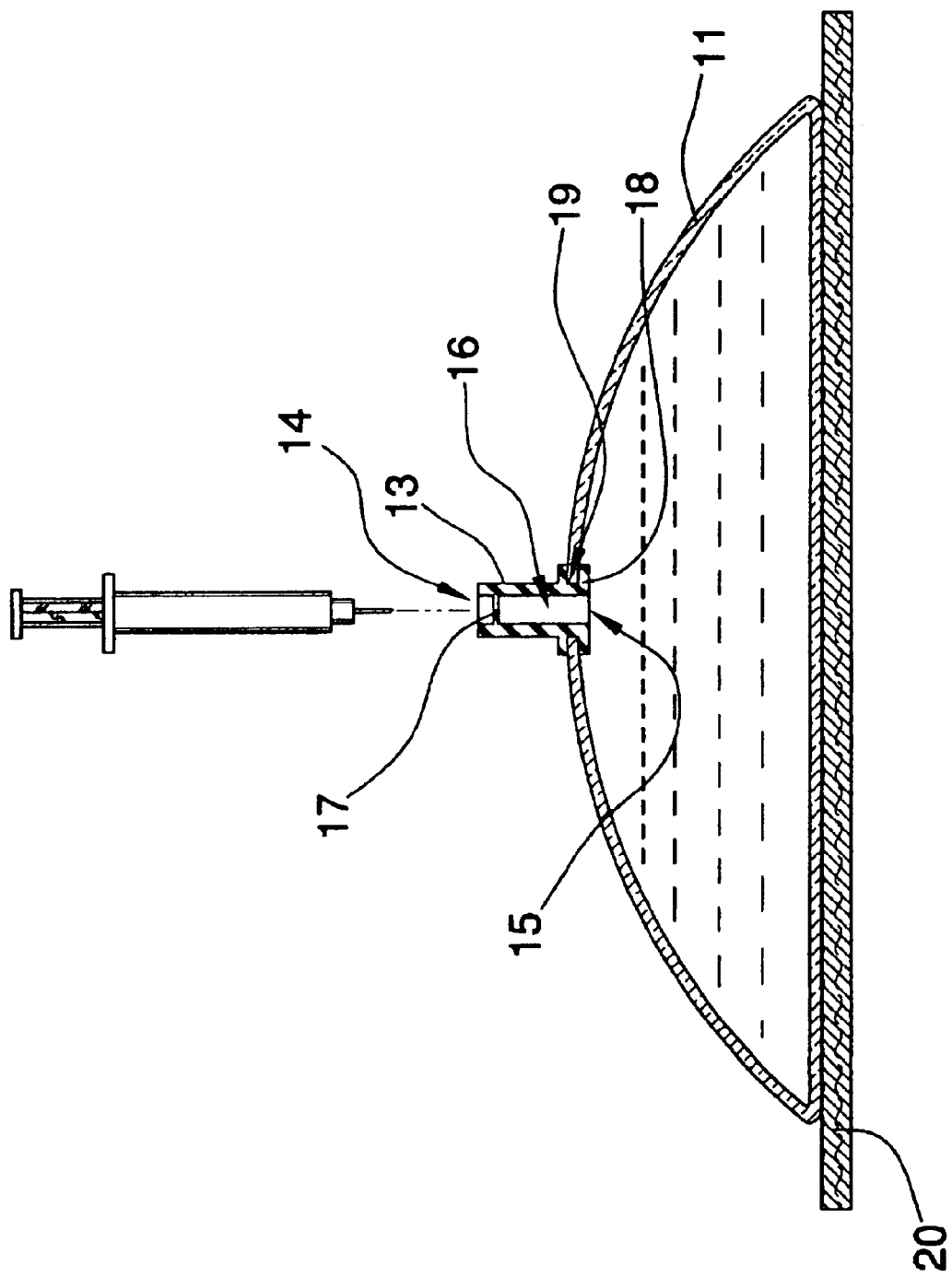
FIG. 4 is a cross-sectional view of the present invention.

With reference now to the drawings, and in particular to FIGS. 1 through 4 thereof, a new abdominal defect cover device embodying the principles and concepts of the present invention and generally designated by the reference numeral 10 will be described.

As best illustrated in FIGS. 1 through 4, the abdominal defect cover device 10 generally comprises a domed-shaped cover member 11 having an opening 12 being centrally-disposed therethrough. The dome-shaped cover member 11 is made of plastic. A valve assembly is securely and conventionally disposed in the opening 12 for allowing introduction of a saline solution upon a user's abdomen via a syringe. The valve assembly includes a tubular member 13 having open ends 14,15 and a bore 16 extending therethrough, and also includes a one-way valve member 17 being conventionally disposed in the bore 16. The tubular member 13 has a base portion 18 having an annular groove 19 being disposed in an exterior thereof and receiving an annular edge defining the opening 12 through the dome-shaped cover member 11 for retaining the tubular member 13 in the opening 12 of the dome-shaped cover member 11.

A seal member 20 is conventionally attached to the dome-shaped cover member 11 for sealing the dome-shaped cover member 11 upon the user's abdomen. The seal member 20 includes an adhesive band and is conventionally attached along and extends outwardly beyond a rim of the dome-shaped cover member 11 to provide a seal between the dome-shaped cover member 11 and the user's abdomen.

A fastening assembly for fastening the dome-shaped cover member 11 upon the user's abdomen includes strap members 21,24 having first ends which are diametrically and conventionally and detachably attached to the seal member 20, and also includes hook and loop fasteners 27,28 being conventionally attached near second ends 23,26 of the strap members 21,24 and also being attached at the first ends of the strap members and to the seal member with the hook and loop fasteners 27,28 at the second ends 23,26 of the strap members 21,24 being fastenable to one another about a user' body to secure the dome-shaped cover member 11 upon the user's abdomen.

In use, the user places the dome-shaped cover member 11 directly upon the effected area of the user's abdomen, and secures the dome-shaped cover member 11 to the user's abdomen using the strap members 21,24. The user can introduce saline upon the effected area of the user's abdomen by using a syringe and injecting the saline through the tubular member 13.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the abdominal defect cover device. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. An abdominal defect cover device comprising:
    a domed-shaped cover member having an opening being centrally-disposed therethrough, said dome-shaped cover member being made of plastic;
    a valve assembly being securely disposed in said opening for allowing introduction of a saline solution upon a user's abdomen, said valve assembly including a tubular member having open ends and a bore extending therethrough, and also including a one-way valve member being disposed in said bore, said tubular member having a base portion having an annular groove being disposed in an exterior thereof and receiving an annular edge defining said opening through said dome-shaped cover member for retaining said tubular member in said opening of said dome-shaped cover member;
    a seal member being attached to said dome-shaped cover member for sealing said dome-shaped cover member upon the user's abdomen; and
    a fastening assembly for fastening said dome-shaped cover member upon the user's abdomen.

2. An abdominal defect cover device as described in claim 1, wherein said seal member includes an adhesive band and is attached along and extends outwardly beyond a rim of said dome-shaped cover member to provide a seal between said dome-shaped cover member and the user's abdomen.

3. An abdominal defect cover device as described in claim 2, wherein said fastening assembly includes strap members having first ends which are diametrically attached to said seal member, and also includes hook and loop fasteners being attached near second ends of said strap members and to said first ends of said strap members and to said seal member, said hook and loop fasteners being attached at said second ends of said strap members being fastenable to one another about a user' body to secure said dome-shaped cover member upon the user's abdomen.

* * * * *